United States Patent [19]

Eibl et al.

[11] 4,048,044

[45] * Sept. 13, 1977

[54] WATER-PURIFYING APPARATUS

[75] Inventors: Volker Eibl; August Reis, both of Munich, Germany

[73] Assignee: Sachs-Systemtechnik GmbH, Schweinfurt am Main, Germany

[*] Notice: The portion of the term of this patent subsequent to Dec. 2, 1992, has been disclaimed.

[21] Appl. No.: 619,696

[22] Filed: Oct. 6, 1975

Related U.S. Application Data

[63] Continuation-in-part of Ser. No. 473,389, May 28, 1974, Pat. No. 3,923,632.

[30] Foreign Application Priority Data

June 9, 1973 Germany .............................. 2329628

[51] Int. Cl.² ........................... C02B 1/82; C02B 3/10
[52] U.S. Cl. .................... 204/257; 204/151; 204/301
[58] Field of Search ................ 204/151, 149, 180 P, 204/180 R, 275, 301, 257, 252; 423/335, 66, 239

[56] References Cited

U.S. PATENT DOCUMENTS

| | | | |
|---|---|---|---|
| 2,046,467 | 7/1936 | Krause | 204/149 X |
| 2,882,210 | 4/1959 | Jenks | 204/151 |
| 3,135,674 | 6/1964 | Ruetschi | 204/151 |
| 3,528,905 | 9/1970 | Miller | 204/149 X |
| 3,923,632 | 12/1975 | Eibl et al. | 204/301 |

Primary Examiner—Arthur C. Prescott
Attorney, Agent, or Firm—Hans Berman

[57] ABSTRACT

In a water purification cell, a silver anode and a cathode have a spacing of 1 to 4 mm. The anode surface and the rate of water flow through the cell are related according to the equation $F \geqq c \times \dot{V}$, wherein F is the anode surface area in cm², $\dot{V}$ is the water flow rate in cm³/second and c is a constant of the dimension sec/cm, with a value of 2 to 5. The density of the current in relation to the area of the anode surface is between 1.5 and 3.0 mA/cm² and the voltage is such that active oxygen is generated at the anode.

4 Claims, 1 Drawing Figure

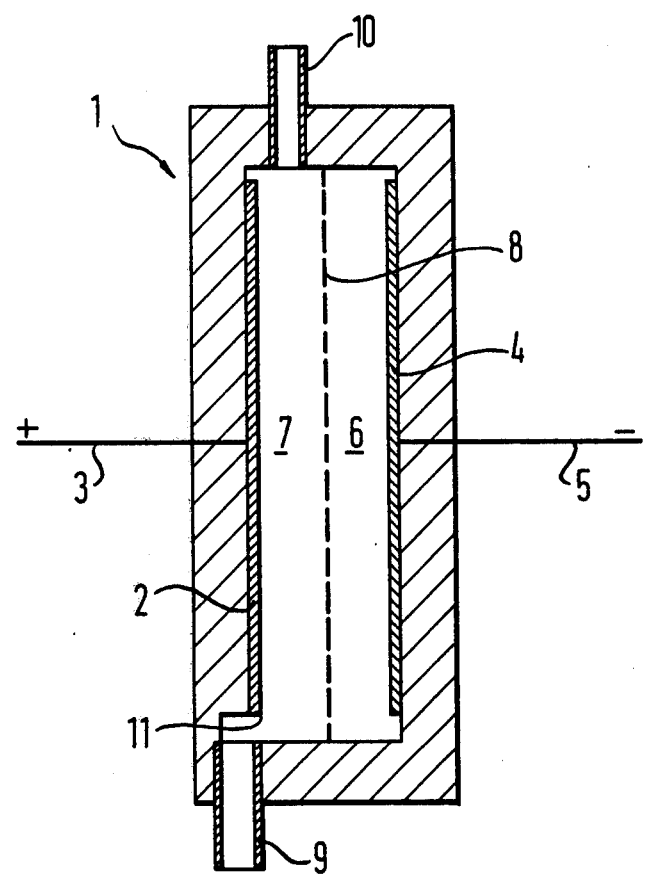

WATER-PURIFYING APPARATUS

This is a continuation-in-part of our copending application Ser. No. 473,389, filed May 28, 1974, now U.S. Pat. No. 3,923,632

The present invention relates to improvements in an apparatus for purifying water contaminated with microorganisms and having a specific resistance in the range of about $0.5 \times 10^3$ ohm . cm to about $6.6 \times 10^3$ ohm . cm. The apparatus is constituted by an electrolytic cell comprising a silver-containing anode and a cathode, and the water to be purified flows substantially parallel to the anode and cathode surfaces through a space therebetween. The anode may be made of a material containing metallic silver or of substantially pure (99%) silver.

The apparatus of this invention avoids the need for disinfective additives whose exact amounts are often difficult to determine and which are frequently inadmissible for the consumption of the water. In the apparatus of the invention, the water is not only disinfected but also decontaminated and detoxicated, bacteriological contaminations being converted into non-toxic compounds.

The above and other objects are accomplished according to the present invention, and water purification may be substantially completed during the passage of the water through the electrolytic cell with an apparatus which comprises a container enclosing a space adapted to hold the water, inlet means for admitting the contaminated water to the space, and outlet means for withdrawing purified water from the space, the space connecting the inlet to the outlet means for permitting the water to flow from the inlet to the outlet means. The space is bounded by the surface of an anode of conductive silver-containing material and the surface of a cathode, the anode and cathode surfaces being substantially parallel to the direction of the water flow between the inlet and outlet means. The space has a width $d$ of about 1 to about 4 mm, preferably up to 2 mm, in a direction perpendicular to the anode surface. The anode surface and the rate of the water flow through the space are related according to the equation $$F \geq c \times \dot{V}$$

wherein $F$ is the area of the anode surface in cm², $\dot{V}$ is the flow rate in cm³/second and $c$ is a constant of the dimension sec/cm, $c$ being at least 2 when $d = 1$ mm, at least 3 when $d = 2$ mm, and at least 5 when $d = 4$ mm, intermediate values of $d$ having parameters derived from linear interpolation between adjacent values of $d$. Leads are connected to the anode and cathode respectively for passing an electric current through the water in the space between the cathode and the anode, the density of the current in relation to the area of the anode surface being in the range of about 1.5 mA/cm² and 3.0 mA/cm², and the voltage being sufficient to generate active oxygen at the anode.

The above-indicated dimensions and relationships have been determined experimentally and, more particularly, it has been found that only within an electrode spacing in the range of 1 to 4 mm is all the water subjected simultaneously to an anodic oxidation and an enrichment with silver ions. While the enrichment with silver ions would be obtained also with a wider spacing, anodic oxidation can be obtained only if the distance between the electrodes does not exceed 4 mm. On the other hand, if the electrodes are spaced closer than 1 mm at the indicated terminal voltage sufficient to generate active oxygen at the anode, more silver ions would enter the water than is tolerable. Silver ion enrichment and anodic oxidation synergistically produce e degree of purification not obtainable otherwise.

Anodic oxidation, as used herein, means the generation of active oxygen at the anode to oxidize any organic matter in the water in the region of the anode. By combining the anodic oxidation with the silver ion enrichment, the dwell time of the water in the electrolytic cell can be reduced to commercially useful periods while producing excellent purification results, i.e. complete sterilization.

The constant $c$ should be limited to the given values to maintain the size of the apparatus within desirable minimum dimensions and to avoid excessively long periods of treatment. The terminal voltage may be between about 1.8 volts and about 12 volts if the space within the electrolytic cell is bounded by the electrode surfaces. The voltage may be higher than 12 volts, if the space is bounded by the anode surface and a diaphragm and the distance between the electrode surfaces is greater than 4 mm.

Other objects, features and advantages of the present invention will become more apparent from the following description of a now preferred embodiment, taken in conjunction with the single FIGURE of the accompanying schematic drawing.

In the drawing, 1 denotes the container of an electrolytic cell comprising anode 2 and cathode 4. Contaminated water is admitted to the space between the anode and cathode surfaces at inlet 9 and purified water is withdrawn from the space at outlet 10, the space connecting the inlet to the outlet for permitting the water to flow from the inlet to the outlet in a direction substantially parallel to the anode and cathode surfaces. As can be seen from the drawing the water inlet 9 is arranged preferably so that the water entering the cell 1 through water inlet 9 is directed first against an edge 11 to create a turbulent flow within the anode compartment 7. Lead 3 is connected to the anode and lead 5 to the cathode. In the illustrated embodiment, the space is divided into anode compartment 7 and cathode compartment 6 by diaphragm 8, which is permeable to anions only, to define the space through which the water flows. However, as indicated by the broken line denoting the diaphragm, the diaphragm may be omitted, in which case the space through which the water flows is defined between the electrode surfaces.

The method of operation of the apparatus is as follows:

The liquid to be disinfected — in the case of the embodiment drinking water — flows through the water inlet 9 into the anode compartment 7 and is subjected there to an oxidation process at the anode due to the current flow between anode 2 and cathode 4. The oxidizing effect, i.e. the removal of electrons, is very effective, for normally badly oxidizing substances are also affected. This is true especially for the microorganisms within the water which are decomposed or at least inactivated by oxidation.

As diaphragm 8 an asbestos sheet can be used, but particularly advantageous results have been obtained with a material only permeable to anions, since in this case a concentration of anions in the anode compartment 7 takes place.

The tests carried out with the silver anode show increased effectiveness as compared to anodic oxidation and of electrolytically precipitated silver. At equal apparatus dimensions and starting from $10^5$ to $10^6$ coli germs per ml, anodic oxidation without a silver anode and treatment with electrolytically precipitated silver without current resulted in a reduction of the number of germs to about $10^3$ to $10^4$ coli per ml after a reaction period of 2 minutes in the test device, a concentration which even upon extension of the reaction period remained substantially constant and, at the most, slightly increased. In comparison tests with silver anodes in the same apparatus with corresponding numbers of germs, no germs could be ascertained after a dwell time of 4 sec. Usually after a dwell time of 2 sec. no germs remained.

The following specific example will further illustrate the practice of this invention. A parallelepiped cell illustrated herein was used, with electrode surfaces having each an area of 6 × 6 cm, the distance $d$ therebetween being 2 mm. Thus, the water flow space between the anode and cathode had a cross section of 6 × 0.2 cm and a volume of 7.2 cm$^3$.

The anode consisted of pure silver (99% silver and 1% impurities) while the cathode consisted of chromium-nickel-molybdenym steel (18% Cr, 11% Ni, 2% Mo).

Munich branch water with a specific resistance of $2.08 \times 10^3$ ohm . cm and a pH of 7.5 was purified in this electrolytic cell. Before treatment, the water was contaminated with E-coli type microorganisms in a concentration of $1.887 \times 10^7$ microorganisms per milliliter. The rate of water flow through the cell was chosen at 6 cm$^3$/second. This water flow rate in the stated cell volume produced a dwell time of 1.2 seconds.

A direct electric current having a voltage of 2.6 V was applied to the electrodes and the generation of active oxygen was noted at the anode. Under the indicated operating conditions, the current density was 2.7 mA per cm$^2$ of the area of the anode surface.

After a single passage of the contaminated water through the cell, no microorganisms were found therein. This was determined in a known manner by inoculating a nutrient medium with the water immediately after it had passed through the cell and subsequently culturing the inoculated medium at 37° C for three days.

What is claimed is:

1. Apparatus for purifying water contaminated with microorganisms and having a specific resistance in the range of about $0.5 \times 10^3$ ohm.cm to about $6.6 \times 10^3$ ohm.cm which comprises:
   a. a container enclosing a space adapted to hold water;
   b. a diaphragm dividing said space into a first compartment and a second compartment and having respective faces in said compartments;
   c. inlet means for admitting said contaminated water to said first compartment;
   d. outlet means for withdrawing purified water from said first compartment;
      1. said first compartment connecting the inlet and outlet means for flow of said water from the inlet means to the outlet means;
   e. an anode of conductive, silver-containing material having a surface in said first compartment substantially parallel to the direction of said flow of water and to the face of said diaphragm in said first compartment at a distance of about 1 mm to about 4 mm from said diaphragm;
   f. a cathode having a surface in said second compartment; and
   g. lead means connected to said anode and to said cathode respectively for passing an electric current between said anode and said cathode through said contaminated water in said first compartment and a conductive liquid in said second compartment.

2. Apparatus as set forth in claim 1, wherein said distance does not exceed 2 mm.

3. Apparatus as set forth in claim 1, wherein the anode is of at least 99% pure silver.

4. Apparatus as set forth in claim 1, wherein the anode forms a part of an inner wall of the container.

* * * * *